United States Patent

Wurzer et al.

[11] Patent Number: 5,849,010
[45] Date of Patent: Dec. 15, 1998

[54] ELECTROSURGICAL APPARATUS AND METHOD FOR ITS OPERATION

[75] Inventors: Helmut Wurzer, Lerchenfeldstr. 10, München, Germany, 80538; Rainer Mäckel, Königswinter, Germany

[73] Assignee: Helmut Wurzer, Munich, Germany

[21] Appl. No.: 558,589

[22] Filed: Oct. 30, 1995

[30] Foreign Application Priority Data

Oct. 31, 1994 [DE] Germany .......................... 44 38 978.7

[51] Int. Cl.⁶ .................................................. A61B 17/39
[52] U.S. Cl. ................................. 606/39; 606/34; 606/41
[58] Field of Search .......................................... 606/32–52

[56] References Cited

FOREIGN PATENT DOCUMENTS

| | | |
|---|---|---|
| 3119735C2 | 1/1983 | Germany . |
| 41266071A1 | 2/1993 | Germany . |
| 4126608A1 | 2/1993 | Germany . |
| 4217999A1 | 12/1993 | Germany . |

*Primary Examiner*—David M. Shay
*Attorney, Agent, or Firm*—Townsend and Townsend and Crew

[57] ABSTRACT

An electrosurgical apparatus has a radio-frequency generator (11) with a variable basic power setting and to which a cutting electrode (12) and a neutral electrode (13) are connected. A power measuring device (15) is connected to the electrodes (12, 13) and acts on a regulating stage (16) which is connected to the power regulating input of the radio-frequency generator (11). The number of sparkovers within a predetermined plural number of periods is determined and is set by regulation of the output power of the radio-frequency generator (11) to a constant value which lies beneath twice the predetermined plural number.

20 Claims, 3 Drawing Sheets

ELECTROSURGICAL APPARATUS AND METHOD FOR ITS OPERATION

This invention relates to controlling a voltage from a radio frequency power supply to avoid flash overs causing charring damage to the flesh. Specifically, both an electrosurgical apparatus and a method for the control of an electrosurgical apparatus is set forth.

The invention can be used both with monopolar and also bipolar instruments.

BACKGROUND OF THE INVENTION

Electrosurgical devices operating with radio-frequency current are known in numerous forms for cutting and/or coagulating human tissue with radio-frequency current. The present invention is concerned with such electrosurgical devices which are either only laid out to execute a radio-frequency current cutting procedure or which can optionally be switched over to the operating mode "cutting" or "coagulating".

In the operating mode "cutting" an arc is generated between the cutting electrode and the which is electrically conductively connected to the neutral electrode at a suitable position. This arc consists of a corresponding number of sparkovers in the frequency of the RF voltage that is used. With a higher power input of the radio-frequency generator a sparkover occurs for each positive and negative half-wave of the radio-frequency current. The frequency of radio-frequency surgical apparatus generally lies in the order or magnitude of 500 KHz. Frequencies below 100 KHz should not be used. A reasonable frequency range extends from approximately 300 KHz to 2 MHz.

It has already become known (DE-OS 25 04 280) to so set the strength of the radio-frequency current by an automatic and adequately rapid regulating procedure that at any time just that power is supplied to the tissue which, on the one hand, ensures a heating of the tissue suitable for the cutting process but, on the other hand, prevents the occurrence of arcs at a damaging level.

It is generally the current strength which is regulated while the voltage provided by the radio-frequency generator is kept substantially constant, at least within the power ranges occurring in operation.

Attempts have already been made to use the DC components which occur during RF cutting, or the harmonics which occur through distortion of the current characteristic, for the regulation of the power of the RF generator. Apart from the relatively high technical cost and complexity for the measurement of the harmonics when using this method the arc has generally already developed too strongly before a counter control can take place through the measurement of the harmonics. The determination of the duration of the current pause between two half-waves can also not provide assistance here because these current pauses first arise at high powers and the arc has then already developed so strongly that the tissue is damaged.

Arcs which are too pronounced, and thus lead to high power being transmitted to the tissue, lead to charring of the cut tissue which in turn makes the healing process more difficult and prolongs it.

SUMMARY OF THE INVENTION

The object underlying the invention is to provide an electrosurgical device and a method for its operation with the aid of which the intensity or the arc or of the sparkovers is automatically reduced to such a value that a problem free cutting process is achieved by means of the cutting electrode, and in particular a cutting process free from adhesion, while at the same time avoiding any form of overheating which goes beyond that of the actual cutting requirement, thus also avoiding charring of the tissue. In particular the electrosurgical apparatus and method of the invention should bring about an automatic and rapid adaptation of the power transmitted by the radio-frequency generator when diverse tissue types (for example muscle tissue or fat) are encountered during the cutting procedure which have different power requirements.

In order to satisfy this object the features of the invention, both a method for the control of the output of a radio frequency power supply and an apparatus utilizing a radio frequency power supply, are provided.

The invention is based on the recognition that in the case of lower powers it is only initially an ohmic or capacitive contact which is present on a first contact between the cutting electrode and the human or animal tissue, where no deviations from the sinusform as yet occur, and that with increasing power sparkovers only initially occur with one type of half-wave of each period, preferably the positive half-waves. This results from the different conditions such as the course of the field, the temperature, the electron affinity at the cutting electrode and at the tissue. During the time course of the radio-frequency current the sparkovers can be recognized as short term increases or peaks. At the same time the voltage at the spark gap can reduce correspondingly if no constant voltage characteristic is used. In the other respective half-wave of a period, preferably the negative half-wave, no substantial deviations from the preset sinusform initially arise with a relatively low power supply. Only with further increasing power supply are first Individual sparkovers and then increasing numbers of sparkovers found during the other half-waves, preferably during the negative half-waves.

The impending occurrence of an arc which is assuming dangerous levels can thus be determined even with a relatively low output power of the radio-frequency generator by the fact that individual sparkovers are found within the positive half-wave. The number of these sparkovers, which can also be termed microarcs can be very rapidly determined with a high dynamic response. The determination of the strength of the arc can thus take place by counting of the sparkovers or microarcs which occur during a predetermined number of periods.

BRIEF DESCRIPTION OF THE DRAWINGS

The invention will now by described in the following by way of example and with reference to the drawings in which are shown.

Figure 1:
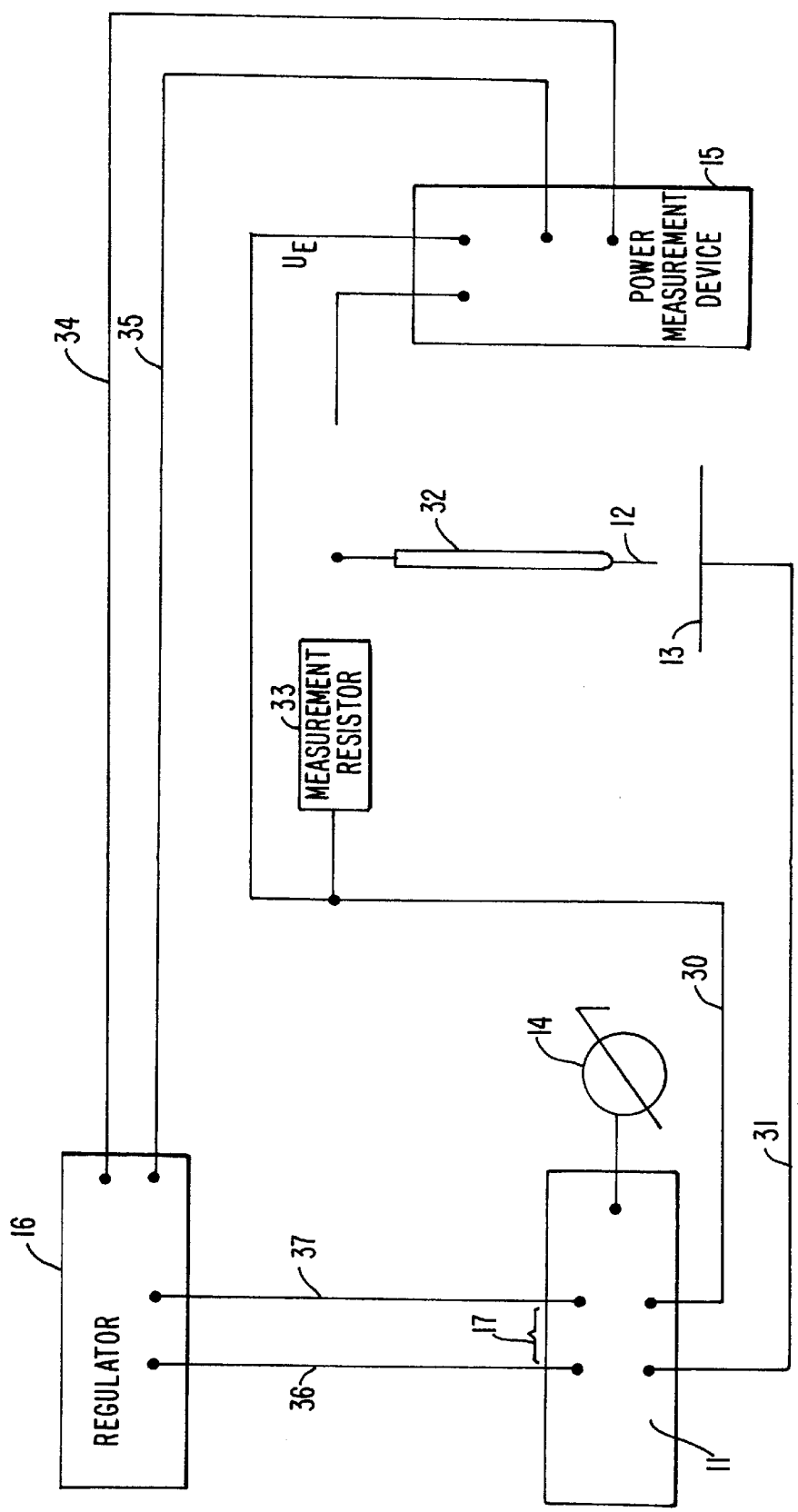
FIG. 1 is an overall view of a radio-frequency surgical device with a radio-frequency generator regulated with respect to its output power.

In accordance with FIG. 1 an RF generator 11, which for example operates at a frequency of 500 KHz, feeds, via lines 30, 31 in which capacitors can be provided for DC decoupling, a radio-frequency surgical cutting instrument with a cutting electrode 12 and a neutral electrode 13 which is to be electrically conductively attached to a suitable position of the body of a patient to be treated.

A setting knob 14 for the selection or a basic power setting is provided at the RF generator 11. By means of this setting knob 14 the surgeon can predetermine a specific strength for the cutting process which is to be carried out, with the regulation in accordance with the invention being so designed that it takes account of this preset power as a maximum value, but reduces it to a greater or lesser degree in the manner of the invention, depending on the requirements of the tissue being treated.

In the feedline 30 to the cutting electrode 12 there is inserted a measurement resistor 33 from the ends of which a voltage $U_E$ is tapped off which is representative for the radio-frequency current flowing to the cutting electrode 12 and which is applied to the input of a power measuring device 15 in accordance with the invention.

The output of the power measuring device 15 is connected via lines 34, 35 to the input of a regulation stage 16 which generates a regulating signal from the detected actual power, with the regulating signal acting via lines 36, 37 on a power regulating input 17 or the radio-frequency generator 11 in such a way that the radio-frequency generator 11, transmits via the output lines 30, 31 the optimum power for the tissue which has just been treated. The radio-frequency generator 11 should preferably operate with substantially constant voltage while the current is regulated for power matching.

The inventive design of the power measuring devise 15 and of the regulating stage 16 will now be described in detail in the following with reference to FIG. 2 and 3.

Figure 2:
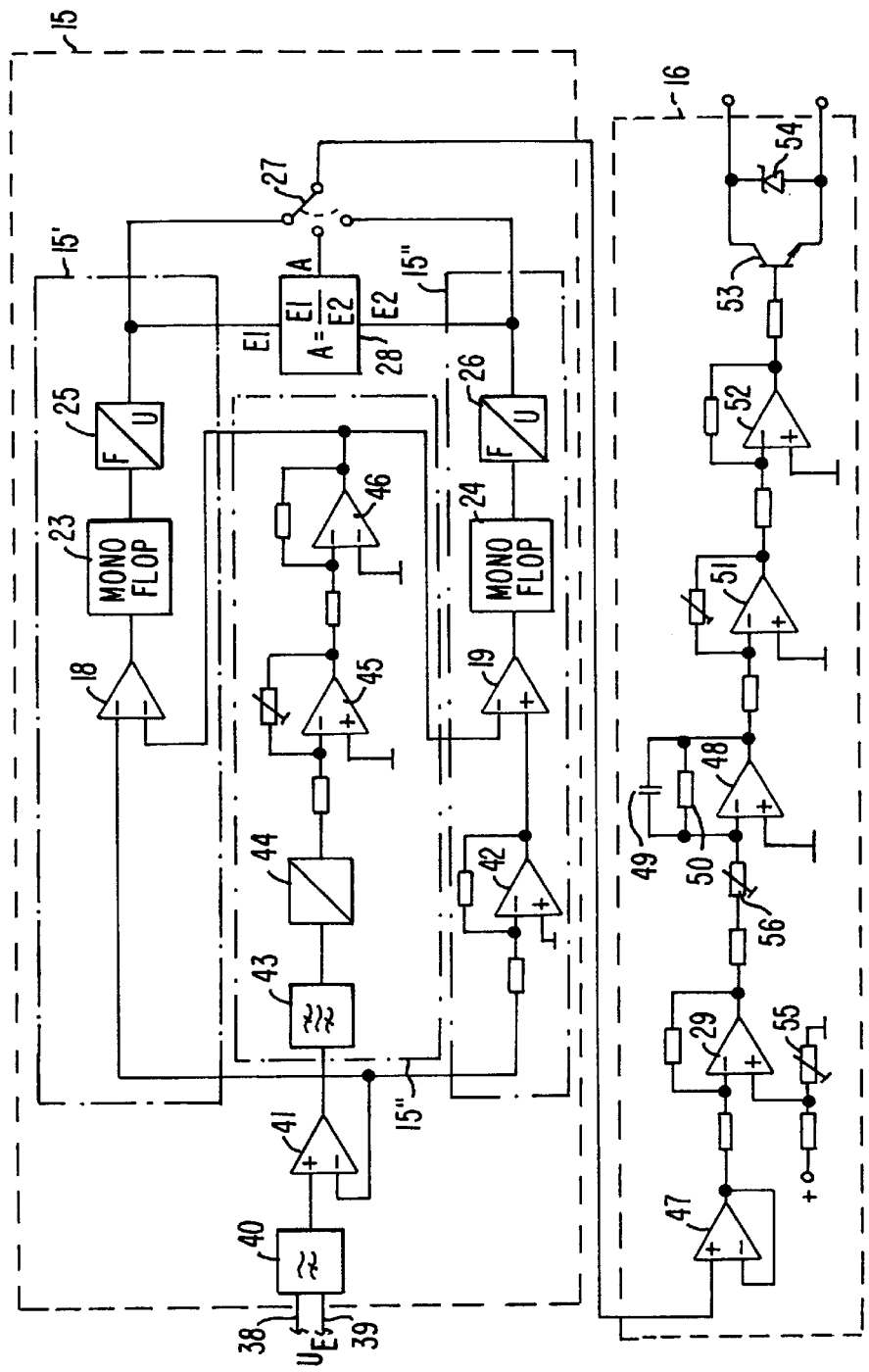
FIG. 2 is a block circuit diagram of an embodiment of a power measuring device in accordance with the invention and of a regulating stage in a radio-frequency surgical device in accordance with FIG. 1.

The voltage $U_E$, proportional to the current through the measurement resistor 33 of FIG. 1 is available in accordance with FIG. 2 at input terminals 38, 39 of the power measuring device 15. It is applied to a high-pass filter 40 which is for example matched, with a frequency of the radio-frequency generator 11 of 500 KHz, to a limiting frequency of 10 KHz. A voltage follower 41 is attached to the output of the high-pass filter 40 and its task lies in preventing back effects of the power measuring device 15 on the patient current circuit.

Two sparkover counting stages 15' and 15" and a reference value generation stage 15''' are connected in parallel to the output or the voltage follower 41.

The sparkover counting stage 15' has a comparator 18 the plus input of which in connected to the output of the voltage follower 41. The comparator 18 acts on a monoflop 23 to which in turn a frequency/voltage converter 25 is connected.

The spark counting stage 15" contains an inverting stage 42 which is acted on by the output of the voltage follower 41 and which inverts the sign of the input signal. The output of the inverting stage 42 is applied to the plus input of a further comparator 19 which is likewise followed by a monoflop 24 to which a frequency/voltage converter 26 is attached.

The reference value generating stage 15''' contains a band-pass filter 43 connected to the voltage follower 41 with the band-pass filter 43 being matched to the frequency of the radio-frequency generator of 500 KHz and being followed by a rectifier/effective value forming stage 44 to which an amplifier 45 is turn connected. The output of the amplifier 45 is applied to an inverting stage 46 at the output of which a reference signal is available which corresponds to the effective value of the radio-frequency voltage averaged over several periods of the radio-frequency voltage multiplied by a predetermined factor.

This reference signal is applied to the minus inputs of the comparators 18 and 19 respectively.

As a result of the described circuit the reference value generator stage 15' evaluates the positive half-waves of the radio-frequency voltage and the reference value generating stage 15" evaluates the negative half-waves of the radio-frequency voltage.

When a positive half-wave of the radio-frequency current generates a larger signal at the plus input of the comparator 18 than the reference value applied to the minus input, then the comparator 18 transmits a pulse to the monoflop 23 which causes the latter to generate a rectangular pulse (TTL signal) the time length (duration) of which is not greater than the time length (duration) of a half-wave of the radio-frequency voltage.

In corresponding manner a negative half-wave triggers via inverting stage 42 an output signal at the comparator 19 when the amplitude of the half-wave is so large that the signal at the plus input or the comparator 19 exceeds the reference value applied to the minus input. Accordingly, the monoflop 24 is set so that it transmits a rectangular pulse (TTL signal) with a length smaller than the length of the half-waves of the radio-frequency voltage.

Depending on how many positive or negative half-waves set the monoflops 23 or 24 respectively, a signal of a higher or lower frequency arises at the output of the monoflop 23, 24 which is converted in the frequency/voltage converters 25, 26 into a voltage signal. The relevant output voltage is applied, on the one hand in each case to a contact of a three position selection switch 27 and, on the other hand, to in each case one input of a logic stage 28, the output of which is connected with the third contact of the three position selection switch 27. The central contact of the three position selection switch 27 is in turn connected to the input of the regulating stage 16.

In the regulating stage 16 a voltage follower 47 is first provided which is again intended to prevent a feedback to the preceding power measuring device 15. It is followed by a differentiating stage 29 to the plus input of which a regulating voltage is supplied as a desired value for the number of sparkovers which is to be kept constant. The regulating voltage can be changed via the regulating resistor 55. A PI regulator 48 is connected to the difference stage 29 via a regulating resistor 56, with the feedback capacitor 49 and feedback resistor so of the PI regulator 48 being so selected that, together with the regulator 56, a time constant results in the millisecond range. The correction time of the PI regulator 48 preferably lies between 0.5 and 10 ms.

The output voltage or the PI regulator 48 is amplified in an amplifier 51 to a desired signal strength and is applied via an inverting stage 52 to a bipolar transistor 53.The bipolar transistor serves as a sink for the regulating input 17 of the RF generator 11 and is applied via the lines 36, 37 of FIG. 1 to the regulating input 17 of the radio-frequency generator 11.

The Zener diode 54 disposed in the output circuit of the bipolar transistor 53 serves to protect the transistor from overvoltage.

The reference value generating stage 15''' of FIG. 2 thus defines a dynamic threshold value which is always greater by a fixed factor than the mean amplitude of the measurement signal. This threshold reference value serves to decide whether a sparkover which is to be counted has occurred or not. If the instantaneous current amplitude is greater than the threshold value, and thus greater than the mean current amplitude multiplied by a fixed factor, then a sparkover which has to be taken into account is present. In order to examine this both the threshold value and also the measurement value are supplied to the comparators 18 and 19 respectively. If the measured value is greater than the threshold value then the comparator 18 or 19 respectively delivers a positive output voltage. It the measurement voltage is smaller than the threshold value then a negative voltage (for example mass potential) is present at the output and no setting of the subsequent monoflop 23 or 24 respectively takes place.

Since the time duration of the sparkovers is short and undefined in relationship to the period of the radio-frequency oscillation short positive voltage pulses arise at the output. In order to give these impulses a defined shape they are supplied to the monoflop 23 or 24 respectively the output pulse width or which (length of the output pulse) is smaller than the half period of the basic oscillation. The so prepared comparator signals are now supplied to the frequency/voltage converters 25 and 26 respectively which effect a conversion of the number of pulses per unit of time into an analog voltage proportional to the number or sparkovers. This voltage serves as a regulating parameter for keeping constant the strength of the arc between the cutting electrode 12 and the neutral electrode 13. It is important that this voltage is monotonic with the coupled in power. In accordance with the invention neither the amplitude nor the time course of the current distortions are evaluated but rather only the frequency of the sparkovers.

This voltage is compared in the desired value comparator 29 with a desired value, is supplied to the PI regulator 48 and is finally coupled back into the radio-frequency generator 11. If the number of sparkovers and thus the current or the voltages is too large than the output power at the generator is reduced via the feedback. If the number of sparkovers is too low than the output power at the radio-frequency generator 11 is increased accordingly.

The manner of operation of the circuit of FIGS. 1 and 2 is as follows:

After switching on the radio-frequency generator 11 the cutting instrument 32 with the cutting electrode 11 is approached towards the tissue of the patient who is connected at a different location and in an electrically conductive manner to the neutral electrode 13. During this an ohmic current initially flows with a sinusoidal shape which does not yet trigger any power limitation of the radio-frequency generator 11 via the power measurement device 15 and the regulating stage 16.

When sparkovers occur with increasing power during some positive half-waves then current peaks arise during these half-waves which set the monoflop 23 when they cause the signal at the plus input of the comparator 18 to be greater than at the reference input (−). They thus cause a corresponding voltage at the output of the frequency/voltage converter 25. The more half-wave sparkovers and thus current peaks which occur the greater is the output voltage of the frequency/voltage converter 25.

With even higher power sparks also arise with the negative half-waves, whereby the monoflop 24 is correspondingly set via the comparator 19 and a voltage corresponding to the number of current peaks or sparks detected is applied to the output of the frequency/voltage converter 26.

In accordance with FIG. 2 the selection switch 26 is applied to the output of the frequency/voltage converter 25 so that its output signal, which is proportional to the number of sparkovers detected in a predetermined time interval, is applied to the input of the regulating stage 16 which forms a regulating signal $U_A$ from it which regulates back the power of the radio-frequency generator 11 when the number of sparkovers which occur during a predetermined number of period of the radio-frequency current is fractionally exceeded. Vice versa the power of the radio-frequency generator 11 is regulated upwardly if too few sparkovers are detected.

By placing the selection switch 27 into the lower position shown in FIG. 2 the output signal of the frequency/voltage converter 26 is applied to the regulating stage 16 so that now the number of sparkovers which occur within the predetermined number of periods for the negative half-waves is responsible for the input signal applied to the input of the regulating stage 16. Depending on how many sparks or current peaks are counted by the sparkover counting stage 15" for the negative half-waves the output signal $U_A$ of the regulating stage 16 regulate the power of the radio-frequency generator 11 upwardly or downwardly. With a constant voltage radio-frequency generator 11 this corresponds to a regulating back of the effective value of the radio-frequency current.

If the selection switch 27 of FIG. 2 is in its middle position the output signal A of the logic circuit 28 is the determining factor acting on the regulating stage 16 and for example forms the quotient E1/E2 of the two output signals of the frequency/voltage converters 25 and 26 respectively.

Figure 3:
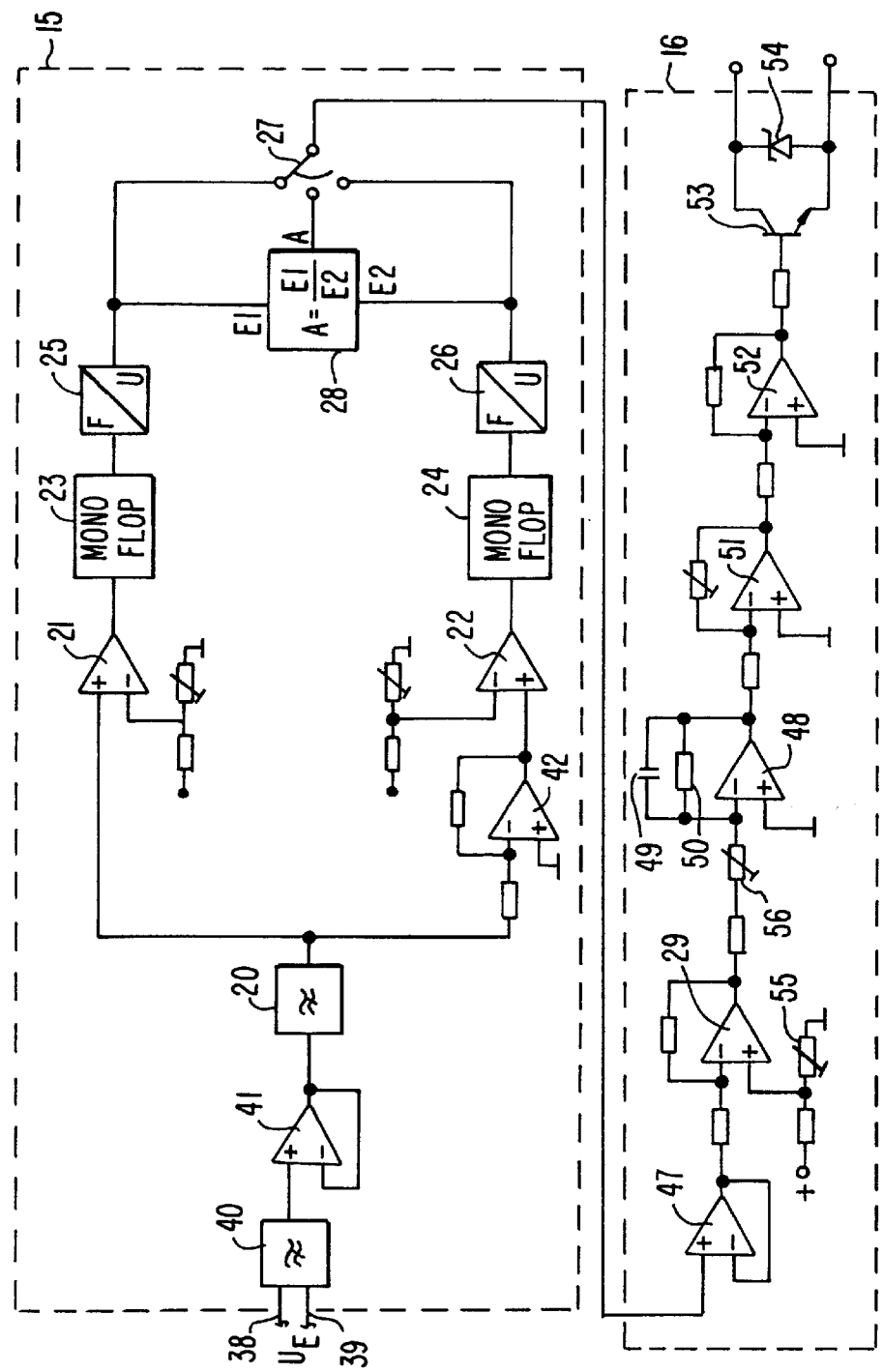
FIG. 3 is a further embodiment of a power measuring device in accordance with the invention with the same regulating stage as is shown in FIG. 2.

In the embodiment of FIG. 3 the same reference numerals are used to designate components corresponding to those in FIG. 2. The circuit is however substantially simplified in comparison to FIG. 2 in that the reference value generation stage 15''' is omitted.

Instead of this a high-pass filter 20 is attached to the output of the voltage follower 41 which is matched to a somewhat higher frequency than that of the radio-frequency generator. If the frequency of the radio-frequency generator amounts to 500 Hz then the high-pass filter 20 should for example be matched to a frequency of 600 KHz.

In this manner it is only the current peaks that are substantially steeper and which occur during the presence of a sparkover during one half-wave which pass through the high-pass filter 20. The signals transmitted during spark formation by the high-pass filter 20 are applied in parallel to a comparator 21 and—via the inverting stage 42—to a comparator 22. The comparators 21,22 are acted on at their reference inputs by a preferably adjustable reference voltage in each case. The voltage is fully selectable and determines the threshold value at which sparkovers are counted when the amplitude exceeds the threshold voltage.

In this manner, when excessive sparkovers form during a positive or negative half-wave corresponding signals arise at the outputs of the comparators 21, 22, as in the example of FIG. 2, are then processed in the same manner via the monoflops 23, 24 and the frequency/voltage converters 25, 26, and are applied to the regulating stage 16 by the selection switch 27, or the logic circuit 28 and the selection switch 27.

The formation of the reference voltage for the comparators 18, 19 in accordance with FIG. 2 thus takes place dynamically by evaluation of the effective value of the current flowing to the cutting electrode 12, with a muiltiplication with a fixed factor taking place in the amplifier 45, whereby the thresholds of the comparators 18 and 19 are first exceeded with a predetermined amplitude of the current peaks.

The voltage at the output of the frequency/voltage converters 25, 26 is monotonic to the number of the sparkovers. Accordingly, the reference value for the comparators 21, 22 or FIG. 3 is preset by a DC voltage, whereas the plus input is subjected by the high-pass filter 20 to a limiting frequency which is higher than the frequency of the RF generator 11.

Instead of the frequency-voltage converters 25 and 26 respectively, a digital counter can also be used, which makes it possible to realize the regulation with a digital regulating circuit.

The centre frequency of the band-pass filter 43 of FIG. 2 corresponds to the operating frequency or the RF generator. Through an adequately high quality factor of the band-pass filter 43 it is ensured that only the basic oscillation and no harmonics are transmitted.

In the embodiment of FIG. 3, instead of determining the mean current amplitude, the basic oscillation is filtered out of the input signal with the aid of the high-pass filter 20. The harmonics are all preserved here. This permits the determination of a static threshold value for the decision as to whether a sparkover is present or not. This threshold value can be generated simply with the aid of a potential divider from the operating voltage.

| Reference Numeral List | |
|---|---|
| 11 | radio-frequency generator |
| 12 | cutting electrode |
| 13 | neutral electrode |
| 14 | adjusting knob for the basic power setting |
| 15 | power measuring device |
| 16 | regulating stage |
| 17 | power regulating input |
| 18 | comparator |
| 19 | high-pass filter |
| 20 | high-pass filter |
| 21 | comparator |
| 22 | comparator |
| 23 | monoflop |
| 24 | monoflop |
| 25 | frequency/voltage converter |
| 26 | frequency/voltage converter |
| 27 | selection switch |
| 28 | logic stage |
| 29 | difference forming stage |
| 30 | line |
| 31 | line |
| 32 | cutting instrument |
| 33 | measurement resistor |
| 34 | line |
| 35 | line |
| 36 | line |
| 37 | line |
| 38 | input terminal |
| 39 | input terminal |
| 40 | high-pass filter |
| 41 | voltage follower |
| 42 | inverting stage |
| 43 | band-pass filter |
| 44 | rectification/effective value forming stage |
| 45 | amplifier |
| 46 | inverting stage |
| 47 | voltage follower |
| 48 | PI regulator |
| 49 | feedback capacitor |
| 50 | feedback resistor |
| 51 | amplifier |
| 52 | inverting stage |
| 53 | bipolar transistor |
| 54 | Zener diode |
| 55 | regulating resistor |
| 56 | regulating resistor |

What is claimed is:

1. The combination of an electrosurgical device for supplying radio frequency power to flesh having:
    a radio frequency generator having a power output;
    a power control input responsive to a variable input for varying the power output of the radio frequency generator;
    a cutting electrode and a neutral electrode connected across the power output of the radio frequency generator, the cutting electrode and the neutral electrode for placement across a body of a patient to cause cutting;
    means for measuring a number of spark overs per unit of time at the cutting electrode;
    means for generating a variable output proportional to the number of spark overs per unit of time; and, means for routing the variable output to the variable input of the power control for varying the power output of the radio frequency generator whereby the power output of the radio frequency generator is responsive to the number of spark overs per unit of time.

2. The combination of an electrosurgical device for supplying radio frequency power to flesh according to claim 1 and further including:
    the means for measuring a number of spark overs per unit of time at the cutting electrode includes measuring short term current increases.

3. The combination of an electrosurgical device for supplying radio frequency power to flesh according to claim 1 and further including:
    the means for measuring a number of spark overs per unit of time at the cutting electrode includes measuring spark gap voltage decreases.

4. The combination of an electrosurgical device for supplying radio frequency power to flesh according to claim 1 and further including:
    the means for generating a variable output proportional to the number of spark overs per unit of time includes generating a voltage signal.

5. The combination of an electrosurgical device for supplying radio frequency power to flesh according to claim 1 and further including:
    the means for measuring a number of spark overs per unit of time at the cutting electrode includes means for deriving an effective current value and measuring a spark over from a current including a current exceeding the effective current value of a current less than the effective current value.

6. The combination of an electrosurgical device for supplying radio frequency power to flesh according to claim 1 and further including:
    the means for measuring a number of spark overs per unit of time at the cutting electrode includes measuring the rate of current change and measuring the number of spark overs exceeding a predetermined rate of change.

7. The combination of an electrosurgical device for supplying radio frequency power to flesh according to claim 1 and further including:
    the means for measuring a number of spark overs per unit of time at the cutting electrode includes utilizing a high pass filter for passing frequencies in excess of a frequency of the radio frequency power supply.

8. The combination of an electrosurgical device for supplying radio frequency power to flesh according to claim 1 and further including:
    the means for measuring a number of spark overs per unit of time at the cutting electrode includes a monoflop; and,
    the means for generating a variable output proportional to the number of spark overs per unit of time includes a frequency to voltage converter.

9. The combination of an electrosurgical device for supplying radio frequency power to flesh according to claim 1 and further including:

the means for measuring a number of spark overs per unit of time at the cutting electrode includes measuring the number of spark over during a positive portion of the power output of the radio frequency generator and measuring the number of spark overs during a negative portion of the power output of the radio frequency generator.

10. In the combination of an electrosurgical device for supplying radio frequency power to flesh according to claim 9 and further including:

the means for generating a variable output proportional to the number of spark overs per unit of time includes utilizing a mathematical relationship between the spark overs during the positive portion and the number of spark overs during the negative portion of the power output of the radio frequency generator, the mathematical relationship being selected from the group consisting of addition, subtraction, multiplication and division.

11. A method of operating an electrosurgical device for flesh to regulate power to prevent damage to the flesh comprising the steps of:

providing a radio frequency generator having a power output;

providing a power control input responsive to a variable input for varying the power output of the radio frequency generator;

providing a cutting electrode and a neutral electrode connected across the power output of the radio frequency generator, the cutting electrode and the neutral electrode for placement across a body of a patient to cause cutting;

measuring a number of spark overs per unit of time at the cutting electrode;

generating a variable output proportional to the number of spark overs per unit of time; and, routing the variable output to the variable input of the power control for varying the power output of the radio frequency generator whereby the power output of the radio frequency generator is responsive to the number of spark overs per unit of time.

12. The method of claim 11 for operating an electrosurgical device for flesh to regulate power to prevent damage to the flesh and comprising the further steps of:

varying the unit of time to include between 3,000 to 8,000 cycles of the radio frequency generator.

13. The method of claim 11 for operating an electrosurgical device for flesh to regulate power to prevent damage to the flesh and comprising the further steps of:

measuring a number of spark overs per unit of time at the cutting electrode includes measuring short term current increases with respect to a threshold current value.

14. The method of claim 11 for operating an electrosurgical device for flesh to regulate power to prevent damage to the flesh and comprising the further steps of:

measuring a number of spark overs per unit of time at the cutting electrode includes measuring spark gap voltage decreases with respect to a threshold voltage value.

15. The method of claim 11 for operating an electrosurgical device for flesh to regulate power to prevent damage to the flesh and comprising the further steps of:

measuring a number of spark overs per unit of time at the cutting electrode includes measuring the number of spark overs during positive portions of the radio frequency generator cycle.

16. The method of claim 11 for operating an electrosurgical device for flesh to regulate power to prevent damage to the flesh and comprising the further steps of:

measuring a number of spark overs per unit of time at the cutting electrode includes measuring the number of spark overs during negative portions of the radio frequency generator cycle.

17. The method of claim 11 for operating an electrosurgical device for flesh to regulate power to prevent damage to the flesh and comprising the further steps of:

measuring a number of spark overs per unit of time at the cutting electrode includes measuring the number of spark overs during positive portions of the radio frequency generator cycle and during negative portions of the radio frequency generator cycle and comparing the number of spark overs during the negative portions and the positive portions in a mathematical relationship selected from the group comprising addition, subtraction, multiplication and division.

18. The method of claim 11 for operating an electrosurgical device for flesh to regulate power to prevent damage to the flesh and comprising the further steps of:

generating a variable output proportional to the number of spark overs per unit of time includes adjusting the level of the variable output proportional to the number of spark overs per unit of time.

19. The method of claim 11 for operating an electrosurgical device for flesh to regulate power to prevent damage to the flesh and comprising the further steps of:

generating the variable output to suppress the power output of the radio frequency generator when the number of spark overs-per-unit time is less than the number of cycles of the radio frequency generator per unit of time.

20. The method of claim 19 for operating an electrosurgical device for flesh to regulate power to prevent damage to the flesh and comprising the further steps of:

generating the variable output to suppress the power output of the radio frequency generator when the number of spark overs-per-unit time is 10% more than the number of cycles of the radio frequency generator per unit of time.

* * * * *